(12) United States Patent
Gupta et al.

(10) Patent No.: US 6,800,757 B2
(45) Date of Patent: Oct. 5, 2004

(54) RED-SHIFTED TRIAZINE ULTRAVIOLETLIGHT ABSORBERS

(75) Inventors: Ram Baboo Gupta, Stamford, CT (US); Hargurpreet Singh, Ansonia, CT (US); Russell C. Cappadona, Norwalk, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/964,919

(22) Filed: Sep. 27, 2001

(65) Prior Publication Data

US 2003/0088098 A1 May 8, 2003

(51) Int. Cl.⁷ ............... C07D 251/12; C07D 251/26; C08K 5/34
(52) U.S. Cl. .............. 544/211; 544/213; 544/217; 544/219; 252/380; 524/100
(58) Field of Search ............... 544/211, 213, 544/217, 219; 252/380; 524/100

(56) References Cited

U.S. PATENT DOCUMENTS

| | | | |
|---|---|---|---|
| 3,118,887 A | * | 1/1964 | Hardy et al. ............ 260/248 |
| 3,244,708 A | | 4/1966 | Duennenberger et al. ... 260/248 |
| 3,843,371 A | | 10/1974 | Piller et al. ............ 96/84 R |
| 3,896,125 A | | 7/1975 | Helmo et al. ........... 260/249.5 |
| 5,786,477 A | | 7/1998 | Waterman .............. 544/215 |
| 5,874,576 A | * | 2/1999 | Huber et al. ............ 544/211 |
| 6,057,048 A | | 5/2000 | Hu et al. ............... 428/690 |
| 6,096,886 A | | 8/2000 | Cohen ................... 544/112 |
| 6,129,908 A | | 10/2000 | Wünsch et al. ........... 424/59 |
| 2001/0020094 A1 | * | 9/2001 | Gupta et al. ............ 544/180 |

FOREIGN PATENT DOCUMENTS

| | | | |
|---|---|---|---|
| GB | 1107143 | * | 1/1967 |
| WO | WO 99/67224 | | 12/1999 |
| WO | WO 99/67226 | | 12/1999 |
| WO | WO 00/14077 | | 3/2000 |
| WO | WO 00/29392 | | 5/2000 |

* cited by examiner

*Primary Examiner*—Richard L. Raymond
*Assistant Examiner*—Venkataraman Balasubramanian
(74) *Attorney, Agent, or Firm*—James A. Jubinsky; Claire M. Schultz; Fran S. Wasserman

(57) ABSTRACT

The present invention relates to novel red-shifted UV absorbers comprising 1,3,5-triazine structures containing a 2-naphthol-derived substituent. The present invention also relates to a method for stabilizing a material by incorporating into such material, e.g., organic material, the novel red-shifted triazine compounds in an amount effective to stabilize the material against the effects of actinic radiation.

19 Claims, No Drawings

RED-SHIFTED TRIAZINE ULTRAVIOLET LIGHT ABSORBERS

FIELD OF THE INVENTION

This invention relates generally to novel red-shifted triazines and their use to protect against degradation by environmental forces, such as actinic radiation, oxidation, moisture, atmospheric pollutants and combinations thereof.

BACKGROUND OF THE INVENTION

Exposure to sunlight and other sources of ultraviolet radiation are known to cause degradation of a variety of materials, especially polymeric materials. For example, polymeric materials such as plastics often discolor and/or become brittle as a result of prolonged exposure to ultraviolet light. Accordingly, a large body of art has been developed directed towards materials, such as ultraviolet light absorbers and stabilizers, which are capable of inhibiting such degradation.

Classes of materials known to be ultraviolet light absorbers are trisaryl-1,3,5-triazines, in which at least one of the aryl rings has a hydroxyl group ortho to the point of attachment to the triazine ring. In general this class of materials is well known in the art. Disclosures of a number of such trisaryl-1,3,5-triazines can be found in the patent literature such as those disclosed in U.S. Pat. Nos. 3,843,371 and 3,896,125.

Typically, the aforementioned phenyl ring with the hydroxyl group ortho to the point of attachment to the triazine ring is based on resorcinol and, consequently, this phenyl ring also contains a second substituent (either a hydroxyl group or a derivative thereof) para to the point of attachment to the triazine ring. For example, U.S. Pat. Nos. 3,118,887 and 3,244,708 disclose p-alkoxy-o-hydroxyphenyl triazines.

This second substituent can be "non-reactive," as in the case of an alkyloxy group, or "reactive" as in the case of a hydroxyalkyloxy (active hydrogen reactive site) or (meth)acryloyl (ethylenic unsaturation reactive site) group.

A general disadvantage of trisaryl-1,3,5-triazines containing a resorcinol group is that they absorb less in the 360–400 nm region than other commercially available UV absorbers, e.g., hydroxyphenyl benzotriazoles. The spectral region from about 360 nm to about 400 nm is commonly known as upper wavelength UV light. An example where protection in the upper UV range is significant is epoxy resins, which are important primers in automotive and other industrial applications. Light can penetrate automotive clear and basecoats and destroy the epoxy primer at the primer/basecoat interface. This is then accompanied by loss of topcoat adhesion, even though the topcoat itself may still be in excellent condition. Exposure to high humidity facilitates this delamination phenomenon.

Increased absorbance in the upper UV region enhances the protection of substrates sensitive to longer wavelength ultraviolet light (near visible), such as primers, coatings, plastics, inks, photographic materials and fibers. Therefore, it is desirable to provide novel triazines with significant UV absorbance extending from the UV region (below about 360 nm in wavelength) into the upper UV region from about 360 nm to about 400 nm.

UV absorbance that is shifted toward the upper UV region is often referred to as red-shifted. This invention discloses novel red-shifted triazines, i.e., those comprising novel 1,3,5-triazine structures containing a 2-naphthol-derived substituent, that have significant UV absorbance in the upper UV region.

SUMMARY OF THE INVENTION

This invention relates to a novel red-shift triazine compound of Formula I:

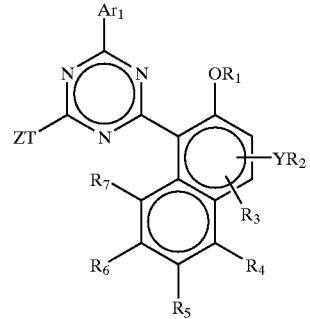

Formula I where $R_1$, $R_2$, are the same or different and each is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, COR, CONRR', and $SO_2R$;

$R_3$, $R_4$, $R_5$, $R_6$ and $R_7$ are the same or different and each is hydrogen, halogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and Y is a direct bond, O, NR", or S, wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 7 to 24 carbons atoms;

T is a direct bond, oxygen, NR' or sulfur, Z is a hydrogen, halogen, substituted or unsubstituted alkyl of 1 to 24 carbon atoms, alkenyl of 2 to 24 carbon atoms, acyl of 1 to 24 carbon atoms, aracyl of 7 to 24 carbon atoms, aryl of 6 to 24 carbon atoms, aralkyl of 7 to 24 carbon atoms, cycloalkyl of 5 to 24 carbon atoms, cycloacyl of 5 to 24 carbon atoms, substituted or unsubstituted alkyl of 1 to 24 carbon atoms interrupted with at least one hetero atom, cycloalkyl of 5 to 24 carbon atoms interrupted with at least one hetero atoms, CONR'''R'''', $SO_2R'''$ or $Ar_2$ wherein R''' is substituted or unsubsti tuted alkyl group of 1 to 24 carbon atoms; R"" is hydrogen or substituted or unsubstituted alkyl group of 1 to 24 carbon atoms;

where $Ar_1$ and $Ar_2$ are each independently a radical of Formula II:

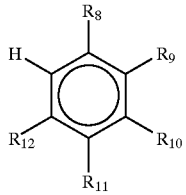

Formula II where $R_8$, $R_9$, $R_{10}$, $R_{11}$, and $R_{12}$ are the same or different and each is hydrogen, halogen, alkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, and optionally with either of $R_8$ and $R_9$, $R_9$ and $R_{10}$, $R_{10}$ and $R_{11}$, or $R_{11}$ and $R_{12}$, taken together being a part of a saturated or unsaturated fused carbocyclic ring optionally containing O, N, or S atoms in the ring. Preferably the radical of Formula II is not a naphthyl substituted with a hydroxyl group ortho to the point of attachment to the triazine ring.

The novel red-shifted triazines of the present invention are particularly useful as ultraviolet light absorber additives for stabilizing a wide variety of materials including, for example, organic compounds, oils, fats, waxes, cosmetics, inks, dyes and biocides, and particularly various organic polymers (both cross-linked and non-cross-linked) used in applications such as photographic materials, plastics, rubbers, paints and other coatings, and adhesives, such as disclosed in a number of the previously incorporated references.

The present invention, consequently, also relates to a method for stabilizing a material by incorporating into such material, e.g., organic material, the inventive red-shifted triazine compounds in an amount effective to stabilize the material against the effects of actinic radiation, and the material so stabilized.

The novel red-shifted triazine compounds of the present invention are also effective as ultraviolet light screening agents in applications such as sunscreens and other cosmetic preparations, capstock layers for extruded polymers and laminated UV-screening window films, among others.

These and other features and advantages of the present invention will be more readily understood by those of ordinary skill in the art from a reading of the following detailed description.

DETAILED DESCRIPTION

This invention relates to a novel red-shift triazine compound Formula I:

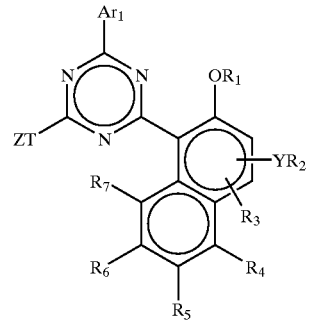

Formula I where $R_1$, $R_2$, are the same or different and each is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, COR, CONRR', and $SO_2R$;

$R_3$, $R_4$, $R_5$, $R_6$ and $R_7$ are the same or different and each is hydrogen, halogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and Y is a direct bond, O, NR", or S, wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 7 to 24 carbons atoms;

T is a direct bond, oxygen, NR' or sulfur, Z is a hydrogen, halogen, substituted or unsubstituted alkyl of 1 to 24 carbon atoms, alkenyl of 2 to 24 carbon atoms, acyl of 1 to 24 carbon atoms, aracyl of 7 to 24 carbon atoms, aryl of 6 to 24 carbon atoms, aralkyl of 7 to 24 carbon atoms, cycloalkyl of 5 to 24 carbon atoms, cycloacyl of 5 to 24 carbon atoms, substituted or unsubstituted alkyl of 1 to 24 carbon atoms interrupted with at least one hetero atom, cycloalkyl of 5 to 24 carbon atoms interrupted with at least one hetero atoms, CONR'"R"", $SO_2R'"$ or $Ar_2$ wherein R'" is substituted or unsubstituted alkyl group of 1 to 24 carbon atoms; R"" is hydrogen or substituted or unsubstituted alkyl group of 1 to 24 carbon atoms.

where $Ar_1$ and $Ar_2$ are each independently a radical of Formula II:

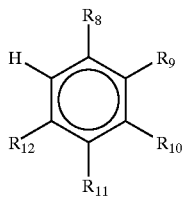

Formula II where $R_8$, $R_9$, $R_{10}$, $R_{11}$, and $R_{12}$ are the same or different and each is hydrogen, halogen, alkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, and optionally with either of $R_8$ and $R_9$, $R_9$ and $R_{10}$, $R_{10}$ and $R_{11}$, or $R_{11}$ and $R_{12}$, taken together being a part of a saturated or unsaturated fused carbocyclic ring optionally containing O, N, or S atoms in the ring. Preferably the radical of Formula II is not a naphthyl substituted with a hydroxyl group ortho to the point of attachment to the triazine ring.

Preferably, the compound of Formula I has the formula below:

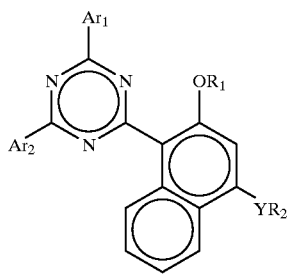

Formula VIII where $Ar_2$ is the same or different as $Ar_1$ as is a radical of Formula II above. More preferably, the compounds of the present invention have Y as a direct bond, and $R_1$ and $R_2$ as hydrogen.

Radicals $Ar_1$ and $Ar_2$ may be any suitable aromatic such as phenyl, methylphenyl, dimethylphenyl, diphenyl, phenyl ether, tetralin, tert-butylphenyl, ethylphenyl, propylphenyl, isopropylphenyl, butylphenyl, isobutylphenyl, chlorophenyl, methoxyphenyl, hydroxyphenyl and combinations thereof.

The novel red-shift triazine compound of the present invention further comprises embodiments of oligomer and dimeric species of Formula III, IV, V, VI, and VII.

Another embodiment of the present invention is oligomeric species of Formula III that has the structure below.

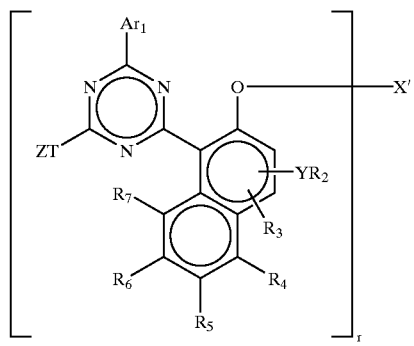

Formula III where T, Z, $Ar_1$, Y, $R_2$ to $R_7$ are defined above;
r is 2 or 3.
when r is 2, X' is $-CO-R^{16}-CO-$, $-CO_2-R^{16}-CO_2-$, $-SO_2-R^{16}-SO_2-$, $-CO-NH-R^{17}-NH-CO-$, a polyoxyalkylene bridge member of formula $-CO-(CH_2)_u-O-(CH_2-(CH_2)_u-O-)_{mm}-(CH_2)_u-CO-$, or $-COC(R^{21})HCH_2NH(C_{nn}H_{2nn}O)_mC_{nn}-H_{2nn}-NHCH_2-C(R^{21})HCO-$
when r=3, X' is:

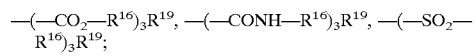

where
$R^{16}$ is $C_2-C_{10}$ alkylene, $C_2-C_{10}$ oxaalkylene or $C_2-C_{10}$ dithiaalkylene, phenylene, naphthylene, diphenylene or $C_2-C_6$ alkenylene;
$R^{17}$ is $C_2-C_{10}$ alkylene, phenylene, naphthylene, methylenediphenylene or $C_7-C_{15}$ alkylphenylene;
$R^{19}$ is $C_3-C_{10}$ alkanetriyl;
$R^{21}$ is hydrogen or $C_1-C_6$ alkyl;
mm is an integer from 2 to 60,
nn is an integer from 2 to 6; and
u is an integer from 1 to 4.

Another embodiment of the present invention is oligomeric species of Formula IV that has the structure below.

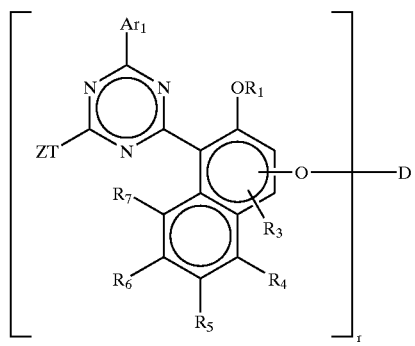

Formula IV wherein T, Z, $Ar_1$, Y, $R_1$ to $R_7$ are defined above;
r is an integer between 2 and 4;
when r is 2, D is selected from the group consisting of $C_2-C_{16}$ alkylene, $C_4-C_{12}$ alkenylene, xylylene, $C_3-C_{20}$ alkylene which is interrupted by one or more oxygen atoms, hydroxy-substituted $C_3-C_{20}$ alkyl which is interrupted by one or more oxygen atoms, $-CH_2CH(OH)CH_2O-R^{15}-OCH_2CH(OH)CH_2$, $-CO-$ $R^{16}$—CO—, —CO—NH—$R_{17}$—NH—CO—, —$(CH_2)_s$—COO—$R^{18}$—OCO—$(CH_2)_s$— a polyoxyalkylene bridge member of the formula XX

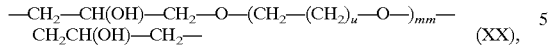
—$CH_2$—$CH(OH)$—$CH_2$—O—$(CH_2$—$(CH_2)_u$—O—$)_{mm}$—$CH_2CH(OH)$—$CH_2$— (XX), a polyoxyalkylene bridge member of the formula XXI

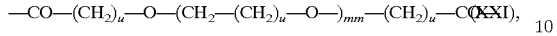
—CO—$(CH_2)_u$—O—$(CH_2$—$(CH_2)_u$—O—$)_{mm}$—$(CH_2)_u$—CO— (XXI), a polyoxyalkylene bridge member of the formula XXII

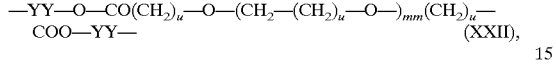
—YY—O—$CO(CH_2)_u$—O—$(CH_2$—$(CH_2)_u$—O—$)_{mm}(CH_2)_u$—COO—YY— (XXII), a polyoxyalkylene bridge member of the formula XXIII

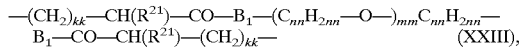
—$(CH_2)_{kk}$—$CH(R^{21})$—CO—$B_1$—$(C_{nn}H_{2nn}$—O—$)_{mm}C_{nn}H_{2nn}$—$B_1$—CO—$CH(R^{21})$—$(CH_2)_{kk}$— (XXIII), a polyoxyalkylene bridge member of the formula XXIV

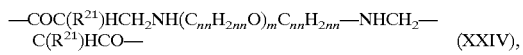
—$COC(R^{21})HCH_2NH(C_{nn}H_{2nn}O)_m C_{nn}H_{2nn}$—$NHCH_2$—$C(R^{21})HCO$— (XXIV), a polyoxyalkylene bridge member of the formula XXV

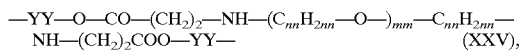
—YY—O—CO—$(CH_2)_2$—NH—$(C_{nn}H_{2nn}$—O—$)_{mm}$—$C_{nn}H_{2nn}$—NH—$(CH_2)_2COO$—YY— (XXV), a polyoxyalkylene bridge member of the formula XXVI

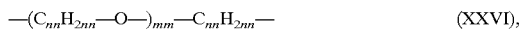
—$(C_{nn}H_{2nn}$—O—$)_{mm}$—$C_{nn}H_{2nn}$— (XXVI), and a polyoxyalkylene bridge member of the formula XXVII

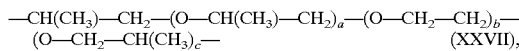
—$CH(CH_3)$—$CH_2$—$(O$—$CH(CH_3)$—$CH_2)_a$—$(O$—$CH_2$—$CH_2)_b$—$(O$—$CH_2$—$CH(CH_3))_c$— (XXVII), wherein a+c=2.5 and b=8.5 to 40.5 or a+c=2 to 33 and b=0,
$R^{21}$ is hydrogen or $C_1$–$C_{16}$ alkyl,
YY is unsubstituted or substituted $C_2$–$C_{20}$ alkyl,
kk is zero or an integer from 1–16,
mm is an integer from 2 to 60,
nn is an integer from 2 to 6,
u is an integer from 1 to 4;
$B_1$ is O or NH;
$R^{15}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl, or phenylene-XX-phenylene wherein XX is —O—, —S—, —$SO_2$—, —$CH_2$—, or —$C(CH_3)_2$—;
$R^{16}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl provided that when r is 3 the alkenyl has at least 3 carbons;
$R^{17}$ is $C_2$–$C_{10}$ alkyl, phenyl, naphthyl, diphenyl, or $C_2$–$C_6$ alkenyl, methylenediphenylene, or $C_4$–$C_{15}$ alkylphenyl; and
$R^{18}$ is $C_2$–$C_{10}$ alkyl, or $C_4$–$C_{20}$ alkyl interrupted by one or more oxygen atoms.
when r is 3, D is —[—$(CH_2)_s$—COO—$]_3$—$R^{19}$
and when r is 4, D is —[—$(CH_2)_s$—COO—$]_4$—$R^{20}$
wherein $R^{19}$ is $C_3$–$C_{10}$ alkanetriyl;
$R^{20}$ is $C_4$–$C_{10}$ alkanetetryl; and
s is 1–6.

Another embodiment of the present invention is the dimeric species of Formula V that has the structure below.

Formula V

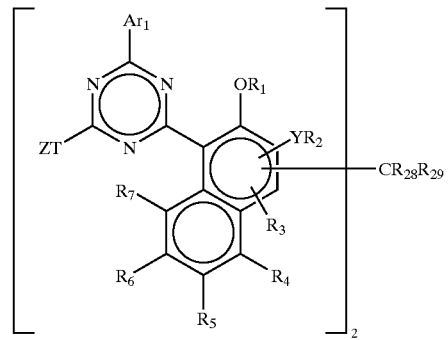

wherein T, Z, $Ar_1$, Y, $R_1$ to $R_7$ are defined above;
and where $R_{28}$ and $R_{29}$ can be the same or different and each is independently a hydrogen, a $C_1$–$C_{20}$ alkyl, an aryl or substituted $C_1$–$C_{20}$ aryl.

Another embodiment of the present invention is oligomeric species of Formula VI that has the structure below.

Formula VI

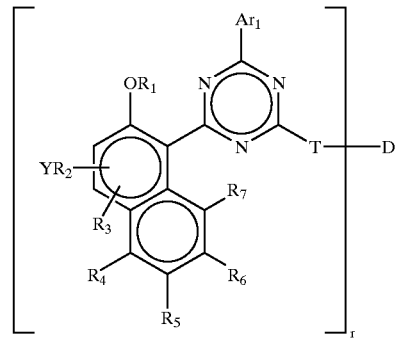

wherein T, $Ar_1$, Y, $R_1$ to $R_7$ are defined above;
r is an integer between 2 and 4;
when r is 2, D is selected from the group consisting of $C_2$–$C_{16}$ alkylene, $C_4$–$C_{12}$ alkenylene, xylyene, $C_3$–$C_{20}$ alkylene which is interrupted by one or more oxygen atoms, hydroxy-substituted $C_3$–$C_{20}$ alkylene which is interrupted by one or more oxygen atoms, —OOC$R^{14}$COO—, —$CH_2CH(OH)CH_2O$—$R^{15}$—$OCH_2CH(OH)CH_2$, —CO—$R^{16}$—CO—, —CO—NH—$R^{17}$—NH—CO—, and —$(CH_2)_s$—COO—$R^{18}$—OCO—$(CH_2)_s$—; and
when r is 3, D is —[—$(CH_2)_s$—COO—$]_3$—$R^{19}$
and when r is 4, D is —[—$(CH_2)_s$—COO—$]_4$—$R^{20}$
wherein $R^{19}$ is $C_3$–$C_{10}$ alkanetriyl and $R^{20}$ is $C_4$–$C_{10}$ alkanetetryl;
s is 1–6;
$R^{14}$ is $C_1$–$C_{12}$ alkyl or phenyl;
$R^{15}$ is $C_2$–$C_{10}$ alkylene phenylene or a phenylene-$X_2$-phenylene- group, wherein $X_2$ is —O—, —S—, —$SO_2$—, —$CH_2$—, or —$C(CH_3)_2$—;
$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;
$R^{17}$ is $C_2$–$C_{10}$ alkylene, phenylene, naphthylene, methylenediphenylene or $C_7$–$C_{15}$ alkylphenylene, and $R^{18}$ is $C_2$–$C_{10}$ alkylene or $C_4$–$C_{20}$ alkylene which is interrupted by one or more oxygen atoms.

Another embodiment of the present invention is oligomeric species of Formula VII that has the structure below.

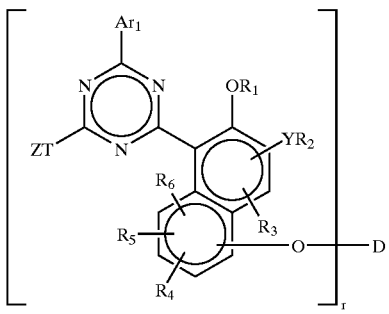

Formula VII where T, Z, $Ar_1$, Y, $R_1$ to $R_7$ are defined above;
r is an integer between 2 and 4;
when r is 2, D is selected from the group consisting of $C_2$–$C_{16}$ alkylene, $C_4$–$C_{12}$ alkenylene, xylylene, $C_3$–$C_{20}$ alkylene which is interrupted by one or more oxygen atoms, hydroxy-substituted $C_3$–$C_{20}$ alkylene which is interrupted by one or more oxygen atoms, —OOCR$^{14}$COO—, —CH$_2$CH(OH)CH$_2$O—R$^{15}$—OCH$_2$CH(OH)CH$_2$, —CO—R$^{16}$—CO—, —CO—NH—R$^{17}$—NH—CO—, and —(CH$_2$)$_s$—COO—R$^{18}$—OCO—(CH$_2$)$_s$—; and
when r is 3, D is —[—(CH$_2$)$_s$—COO—]$_3$—R$^{19}$
and when r is 4, D is —[—(CH$_2$)$_s$—COO—]$_4$—R$^{20}$
wherein $R^{19}$ is $C_3$–$C_{10}$ alkanetriyl and $R^{20}$ is $C_4$–$C_{10}$ alkanetetryl;
s is 1–6;
$R^{14}$ is $C_1$–$C_{12}$ alkyl or phenyl;
$R^{15}$ is $C_2$–$C_{10}$ alkylene phenylene or a phenylene-$X_2$-phenylene- group, wherein $X_2$ is —O—, —S—, —SO$_2$—, —CH$_2$—, or —C(CH$_3$)$_2$—;
$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;
$R^{17}$ is $C_2$–$C_{10}$ alkylene, phenylene, naphthylene, methylenediphenylene or $C_7$–$C_{15}$ alkylphenylene, and
$R^{18}$ is $C_2$–$C_{10}$ alkylene or $C_4$–$C_{20}$ alkylene which is interrupted by one or more oxygen atoms.

In the above oligomer and dimeric formulas III to VII, it is preferable that radicals $R_3$ to $R_7$ are hydrogen. More preferably, the compounds of the formulas III to VII have Y as a direct bond and $R^1$ and $R_2$ as hydrogen, or Y as an oxygen and $R_2$ as a $C_1$ to $C_{24}$ alkyl and $R_1$ as hydrogen. In addition it is preferable that T is a direct bond and Z is the radical $Ar_2$.

Radicals $Ar_1$ and $Ar_2$ for the compounds of Formula III to VII may be any suitable aromatic such as phenyl, methylphenyl, dimethylphenyl, diphenyl, phenyl ether, tetralin, tert-butylphenyl, ethylphenyl, propylphenyl, isopropylphenyl, butylphenyl, isobutylphenyl, chlorophenyl, methoxyphenyl, hydroxyphenyl and combinations thereof.

The triazines of the present invention may optionally have the added benefit of being capable of being chemically bonded to appropriate polymer systems via functionality attached to the triazine groups (e.g., by a hydroxyl, ethylenic unsaturated and/or activated unsaturated group in one or more of Y or Z).

The triazines of the present invention may in general be prepared via a number of procedures well known in the art, for example, those described in Brunetti, H; Luethi, C.; *Helv. Chemica Acta*, 55 (1972) pp.1566–1595; Tanimoto, S.; Yamagata, M. *Senryo to Yakahin*, 40 (1995) pp 339ff; U.S. Pat. Nos. 5,106,972; 5,288,868; 5,438,138 and 5,478,935; EP 395,938; EP 577,559; EP 649,841; EP 779,280; WO 9,628,431; GB 884,802; WO 00/29392 and Japanese Patent Kokai Tokkyo Koho 9,059,263 all of which are incorporated herein by reference for all purposes as if fully set forth. The preferred method is the procedure in WO/29392.

The novel triazines of the present invention are particularly useful as ultraviolet light absorber agents for stabilizing a wide variety of materials including, for example, organic compounds, oils, fats, waxes, cosmetics, inks, dyes and biocides, and particularly various organic polymers (both cross-linked and non-cross-linked) used in applications such as photographic materials, plastics, fibers or dyed fibers, rubbers, paints and other coatings, and adhesives. The present invention, consequently, also relates to (1) a method of stabilizing a material which is subject to degradation by actinic radiation (e.g., an organic material such as an organic polymer in the form of a film, fiber, shaped article or coating) by incorporating into said material an amount of an actinic radiation stabilizer composition effective to stabilize the material against the effects of actinic radiation, wherein the actinic radiation stabilizer composition comprises the inventive triazines; and (2) the material so stabilized.

The novel triazines of the present invention are also effective as ultraviolet light screening agents in applications such as sunscreens and other cosmetic preparations, capstock layers for extruded polymers, dyed fibers and laminated UV-screening window films. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount effective to reduce the amount of actinic radiation impinging on the substrate, wherein the actinic radiation screening composition comprises the inventive triazines; and (2) the substrate so protected.

The novel triazines of the present invention may also be employed to form light stabilizing compositions. Such light stabilizing compositions may include a variety of other components known in the art including other ultraviolet light absorbers of the triazine class, other ultraviolet light absorbers of different classes (e.g. benzotriazoles, benzophenones), hindered amine light stabilizers, radical scavengers, antioxidants and the like.

Methods of Preparation

The method of preparing the novel triazines of the present invention can be preformed by any suitable method as mentioned above. Preferably, the method of producing the novel triazine compound is from the method described in WO 00/29392 herein incorporated by reference in its entirety.

The term "Lewis acid" is intended to include aluminum halides, alkylaluminum halides, boron halides, tin halides, titanium halides, lead halides, zinc halides, iron halides, gallium halides, arsenic halide, copper halides, cadmium halides, mercury halides, antimony halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, or a mixture thereof.

As used herein the term "reaction promoter" is understood to comprise a compound which is used in combination with the Lewis acid to facilitate the reaction. Suitable reaction promoters include acids, bases, water, alcohols, aliphatic halides, halide salts, acid halides, halogens, alkenes, alkynes, ester, anhydride, carbonate, urethane, carbonyl, epoxy, ether, acetal compounds, or mixtures thereof. For a more detailed list of reaction promoters, refer to WO 00/29392.

The novel triazines of the present invention can be prepared through the modified Friedel-Crafts reaction of a cyanuric halide with an aromatic compound of Formula II in the presence of a reaction promoter and a Lewis acid to first produce intermediate bisaryl triazine derivative, (see Scheme 1), followed by or reacted concurrently with a 2-naphthol based compound.

about 2 to about 4 mol equivalents to cyanuric halide. The preferred Lewis acid is aluminum chloride.

Advantageously, a reaction promoter can be used in conjunction with a Lewis acid when synthesizing the desired compounds. Preferably, the amount of reaction promoter should be between about 0.01 to about 5 mol equivalents, or about 0.1 to about 2 mol equivalents. The reaction should run for a sufficient amount of time, at a sufficient temperature and pressure to synthesize the desired triazine. The preferred reaction time for the synthesis of the intermediate compound, i.e., the first step, is between about 5 minutes and about 48 hours, more preferred between about 15 minutes and about 24 hours. The preferred reaction time for the synthesis of end product compound, i.e., the second step, is

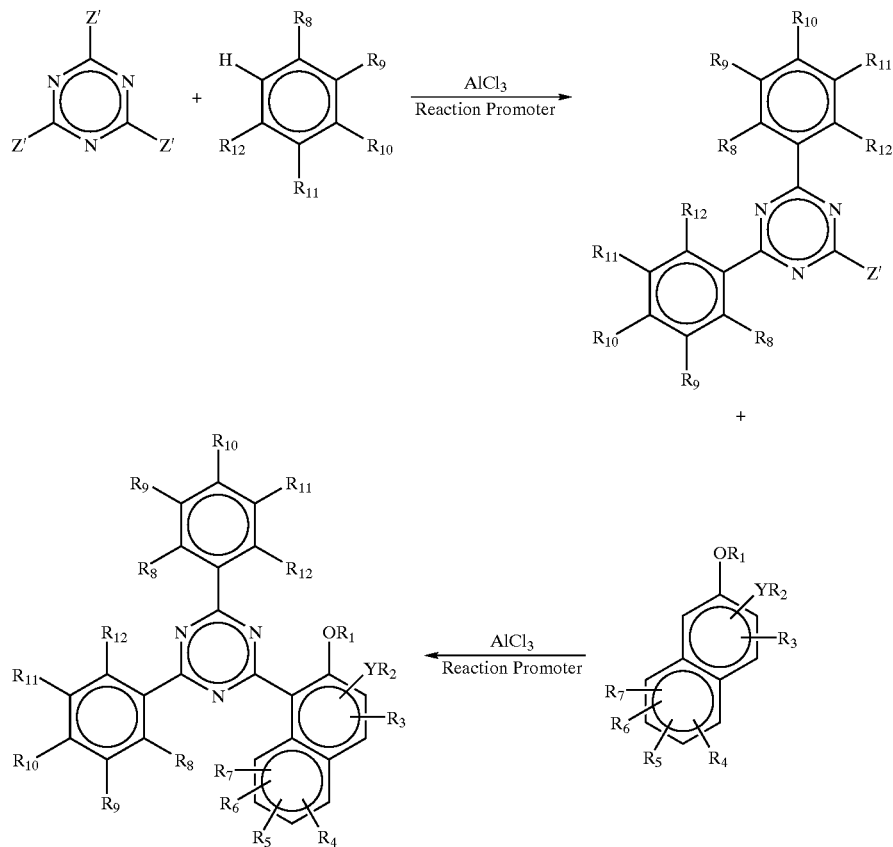

Scheme 1 wherein Z' is bromine, chlorine, fluorine or iodine and the other substituents are defined above.

The relative amounts of the reactants are as follows. The amount of aromatic compounds of Formula II should be in sufficient amounts to react with the cyanuric halide to produce the desired intermediate compound. Preferably, about 2 molar equivalents of the compound of Formula II should be reacted with the cyanuric halide to obtain intermediate bisaryl triazine derivative.

The amount of Lewis acid, such as $AlCl_3$, used in the reaction should be in sufficient amounts to transform the cyanuric halide to the desired intermediate and/or end product. The amount of Lewis acid should be between about 0.5 to about 500 mol equivalents to the cyanuric halide. Preferably, the amount of Lewis acid should be between about 1 to about 5 mol equivalents to the cyanuric halide or between about 10 minutes and about 24 hours, more preferably time is between about 30 minutes and about 12 hours. The preferred reaction temperature for the first step is between about −50° C. and about 150° C., more preferred reaction temperature between about −30° C. and about 50° C. The reaction pressure is not critical and can be about 1 atmosphere or higher if desired. Preferably, the reaction is carried out under an inert gas such as nitrogen or argon. The preferred reaction temperature for the second step is between about 0° C. and about 120° C., a more preferred reaction temperature is between about 20° C. and about 100° C.

The step-wise process comprises mixing at least one Lewis acid, at least one reaction promoter, cyanuric halide and the aromatic compound of Formula II, preferably until the reaction is between about 70% to about 100% completed. Thereafter, the bisaryl triazine product is isolated and purified. The intermediate product is then added to the purified product along with Lewis acid and optionally a reaction promoter to synthesize the desired end product. The step-wise sequence allows for the isolation, purification, and storage of compounds of the intermediate prior to subsequent reaction with 2-naphthol-based compounds.

The continuous reaction comprises allowing the cyanuric halide to react with one or more aromatic compounds of Formula II in the presence of at least one Lewis acid and at least one reaction promoter preferably until the reaction is between about 70% to about 100% complete. Thereafter, without isolating the intermediate product, the 2-naphthol-based compound is allowed to react with the intermediate product in the presence of optionally at least one second Lewis acid and optionally at least one second reaction promoter preferably until the reaction is between about 70% to about 100% complete. The continuous reaction eliminates the need to purify the intermediate product or use of additional reagents such as solvents, and optionally Lewis acids and acids. Moreover, the one-step process simplifies the synthetic reaction pathway such that no unnecessary handling or processing of the reaction mixture is required until the reaction is completed.

Uses of the Triazines

As indicated earlier, the novel triazines of the present invention are particularly useful as ultraviolet light absorber agents for stabilizing a wide variety of materials including, for example, various polymers (both cross-linked and thermoplastic), photographic materials and dye solutions for textile materials, as well as in ultraviolet light screening agents (such as sunscreens). The novel triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the triazines of the present invention can be employed to stabilize materials which are subject to degradation by ultraviolet radiation by incorporating the presently claimed compounds into a composition comprising polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfides, PPO, polysulfones, polyethersulfones, polyvinylchlorides, polycarbonates, polyketones, aliphatic polyketones, thermoplastic TPO's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

The preferred polymeric material is selected from the group consisting of polyolefins; copolymers of one or more monoolefins and/or diolefins with carbon monoxide and/or with other vinyl monomers; hydrocarbon resins (such as $C_5$–$C_9$) including hydrogenated modifications thereof and mixtures of polyalkylenes and starch; polyesters; copolyethers esters; polyethers; polyketones; polyamides and copolyamides derived from diamines, dicarboxylic acids and/or aminocarboxylic acids or the corresponding lactams; natural and synthetic rubbers and elastomers; polyurethanes; polystyrenes, poly-α-methylstyrenes and copolymers with other vinyl monomers; graft copolymers of styrene; high impact polystyrenes; polyacrylic acids, polymethacrylics acids, polyacrylates, polymethacrylates, polyacrylamides, polyacrylonitriles; homo- and copolymers derived from unsaturated alcohols and amines or the acyl derivatives or acetals thereof such as polyvinyl alcohol, polyvinyl acetate, polyacetals, and polybutyrals; homo- and copolymers of cyclic ethers such as alkylene glycols and alkylene oxides, as well as copolymers with bisglycidyl ethers; polybutadienes; polystyrenes; ABS (acrylonitrile butadiene styrene); SAN (styrene acrylonitrile); ASA (acrylate styrene acrylonitrile); cellulosic acetate butyrate; cellulosic polymers; polyureas; polyimides; polyamides-imides; polyester-imides; polyether-imides; polyhydantoins; polybenzimidazoles; polyphenylsulfide; PPO (polypropylene oxide); polysulfones; polyether sulfones; polyether ketones; halogen-containing polymers; polyvinylchlorides; polycarbonates; polyester carbonates; thermoplastic TPO's; amino resin cross-linked polyacrylates and polyesters; polyisocyante cross-linked polyesters and polyacrylates; phenol/formaldehyde, urea/formaldehyde and melamine/formaldehyde resins; saturated and unsaturated polyester resins; cross-linkable acrylic resins derived from substituted acrylates such as epoxy acrylates, hydroxy acrylates, isocyanato acrylates, urethane acrylates or polyester acrylates; alkyd resins, polyester resins, and acrylate resins cross-linked with melamine resins, urea resins, isocyanates, isocyanurates, carbamates, or epoxy resins; cross-linked epoxy resins derived from aliphatic cycloaliphatic, heterocyclic and/or aromatic glycidyl compounds which are cross-linked with anhydrides or amines; polysiloxanes; Michael addition polymers of amines or blocked amines (e.g., ketimines) with activated unsaturated and/or methylene compounds; of ketimines with activated unsaturated and/or methylene compounds such as acrylates and methacrylates, maleates, and acetoacetates; polyketimines in combination with unsaturated acrylic polyacetoacetate resins or with unsaturated acrylic resins; radiation curable compositions; epoxymelamine resins; natural polymers such as cellulose, rubber, gelatin, and chemically modified derivatives thereof; organic dyes and pigments; any mixture or blends of the above; cosmetic products; cellulose-based paper formulations; photographic film; paper; ink; and intraocular lenses.

The amount of the triazine compound of the present invention needed to stabilize the material is typically about 0.1 to about 20% by weight based on the weight of the material to be stabilized and preferably about 0.2% to about 10%, or about 0.5% to about 5% by weight.

Depending upon their ultimate end use, the triazines of the present invention may be combined with a variety of additives conventionally employed in the UV stabilizing art such as anti-oxidants, UV absorbers and stabilizers, metal deactivators, phosphites and phosphonites, hydroxylamines, nitrones, thiosynergists, co-stabilizers, nucleating agents, fillers and reinforcing agents, plasticizers, lubricants, emulsifiers, pigments, rheological additives, catalysts, level agents, optical brighteners, flameproofing agents, anti-static agents and blowing agents. Examples of these additives may be found, for example, in U.S. Pat. No. 6,096,886, herein incorporated by reference in its entirety. Further examples are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Especially preferred are other UV stabilizers and antioxidants including, but not limited to 2-(2'-hydroxyphenyl) benzotriazoles, oxamides, 2-(2-hydroxphenyl)-1,3,5-triazines, 2-hydroxybenzophenones, sterically hindered amines and hindered phenol antioxidants.

Examples of such anti-oxidants and UV stabilizers are: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl) benzotriazole; 2-(3',5'-di-tert-amyl-2'-hydroxphenyl) benzotriazole; 2-(3',5'-bis($\alpha,\alpha$-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; [R—CH$_2$CH—COO(CH$_2$)$_3$]$_2$ B where R=3'-tert-butyl-4'-hydroxy-5'-2H-benzotriazol-2-ylphenyl; bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis (2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis (2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy) phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/ tridecyloxy-2-hydroxypropoxy)-2-hydroxyphenyl]-4,6-bis (2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy) phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxy- benzophenone; 2-hydroxy-4-dodecyloxybenzophenone; 2-hydroxy-4-benzyloxybenzophenone, 4,2',4-trishydroxy-benzophenone; 2'-hydroxy-4,4'-dimethoxybenzophenone; 1,3,5-tris(2,6-dimethyl-4-tert-butyl-3hydroxybenzyl) isocyanurate; 1,3,5-tris(3,5-di-tert-butyl-4-hydroxybenzyl) isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of $\beta$-(3,5-di-tert-butyl-4-hydroxyphenyl)propionic acid with mono- or polyhydric alcohols; esters of $\beta$-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of $\beta$-(3,5-di-tert-butyl-4-hydroxyphenyl)propionic acid such as N,N'-bis(3,5-di-tert-butyl-4-hydroxyphenylpropionyl) hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

The weight ratio of the triazine compounds of the present invention to the other additives, such as the preferred additives may be, for example from about 500:1 to about 1:500, or about 100:1 to about 1:100, or about 10:1 to about 1:10. The novel triazines of the present invention can also be employed in multilayer systems. In such systems, a polymer composition having from about 0.1 to about 20% by weight and preferably a relatively high content of novel trizaine stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by co-extrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of an UV filter, which protects the interior of the article from UV light. The outer layer preferably contains about 0.1 to about 20%, preferably about 1 to about 15%, and most preferably about 2 to about 10% by weight of the outer layer composition, of at least one of the triazine compounds of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel triazine compounds can be used as stabilizers for coatings, for example for paints such as disclosed in numerous references (see, e.g., U.S. Pat. Nos. 4,619,956; 4,740,542; 4,826,978; 4,962,142; 5,106,891; 5,198,498; 5,298,067; 5,322,868; 5,354,794; 5,369,140; 5,420,204; 5,461,151; 5,476,937; EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the presently claimed triazines of the present invention.

To achieve maximum light stability, it is of particular interest to add sterically hindered amines. This invention therefore also relates to a coating composition which, in addition to the binder, the novel triazines and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

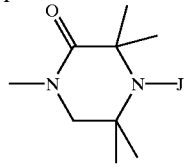

in which J is, for example, hydrogen, hydroxyl, alkyl (such as methyl), alkoxy (such as methoxy) or acyl.

More preferably the stabilizer is a 2,2,6,6-tetraalkylpipieridine derivative containing at least one group of the formula:

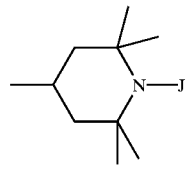

in which J is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933; 4,344,876; 4,426,471; 4,426,472; 4,619,956; 5,004,770; 5,006,577; 5,064,883; 5,112,890; 5,124,378; 5,106,891; 5,204,473 and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):

bis(2,2,6,6-tetramethylpiperid-4-yl) succinate,
bis(2,2,6,6-tetramethylpiperid-4-yl) sebacate,
bis(1,2,2,6,6-pentamethylpiperid-4-yl) sebacate,
di(1,2,2,6,6-pentamethylpiperid-4-yl) butyl-(3,5-di-tert-butyl-4-hydroxybenzyl)malonate, bis(1-octyloxy-2,2,6,6-tetramethylpiperid-4-yl) sebacate, tetra(2,2,6,6-tetramethylpiperid-4-yl) butane-1,2,3,4-tetracarboxylate, tetra(1,2,2,6,6-pentamethylpiperid-4-yl) butane-1,2,3,4-tetracarboxylate, 2,2,4,4-tetramethyl-7-oxa-3,20-diaza-21-oxo-dispiro[5.1.11.2]heneicosane, and
8-acetyl-3-dodecyl-1,3,8-triaza-7,7,9,9-tetramethylspiro [4.5]decane-2,4-dione. Commercially available examples of these and other tetraalkylpipieridine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASORB® UV-3346, UV 3529, UV-3853, UV-500 and UV-516 (Cytec Industries Inc.).

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

For more detailed examples of these and other uses for UV stabilizers, such as the triazines of the present invention, see U.S. Ser. No. 09/335,886, filed on Jun. 18, 1999, (WO 99/67226, pages 33 to 81), herein incorporated by reference.

The invention will now be illustrated by the following examples. The examples are not intended to be limiting of the scope of the present invention. In conjunction with the general and detailed descriptions above, the examples provide further understanding of the present invention.

EXAMPLES

Examples and reaction schemes for producing specific examples of 2-naphthol substituted triazines in accordance with the invention are provided below. While the following examples illustrate preparations with a limited variety of aromatic compounds and 2-naphthol, one of ordinary skill will understand that these reactions may also be carried out with any of a variety of other aromatic and substituted 2-naphthol compounds.

Example 1

Preparation of 2,4-bis(4-phenoxyphenyl)-6-(2-hydroxynaphthyl)-1,3,5-triazine

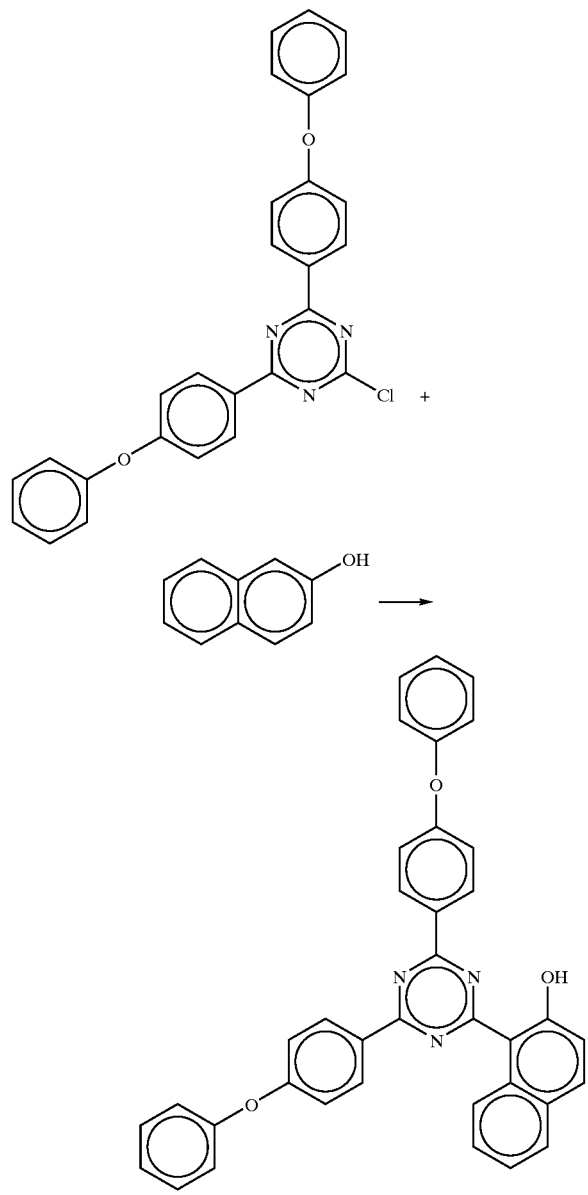

In a 2-neck round bottom flask equipped with a magnetic stirring bar, a condenser and a nitrogen inlet was added 0.9 g of 2,4-bis(4-phenoxyphenyl)-6-chloro-1,3,5-triazine (prepared by following the process disclosed in WO 00/29392, viz., by reacting cyanuric chloride with phenyl ether in the presence of aluminum chloride and concentrated HCl and isolating it) followed by 5 ml chlorobenzene and 0.32 g of 2-naphthol. To it was then added 0.4 g AlCl$_3$ and the reaction mixture heated at 70° C. for 3 hours. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give 1.1 g of a product identified to be 2,4-bis(4-phenoxyphenyl)-6-(2-hydroxynaphthyl)-1,3,5-triazine on the basis of HPLC, NMR and mass spectroscopy. The UV spectrum confirmed it to be a red-shifted UV absorber: $\lambda_{max}$ (nm) 280 ($\epsilon$: 62696); 319 ($\epsilon$: 53925); and 383 ($\epsilon$: 14289).

Example 2

Preparation of 2,4-diphenyl-6-(2-hydroxynaphthyl)-1,3,5-triazine

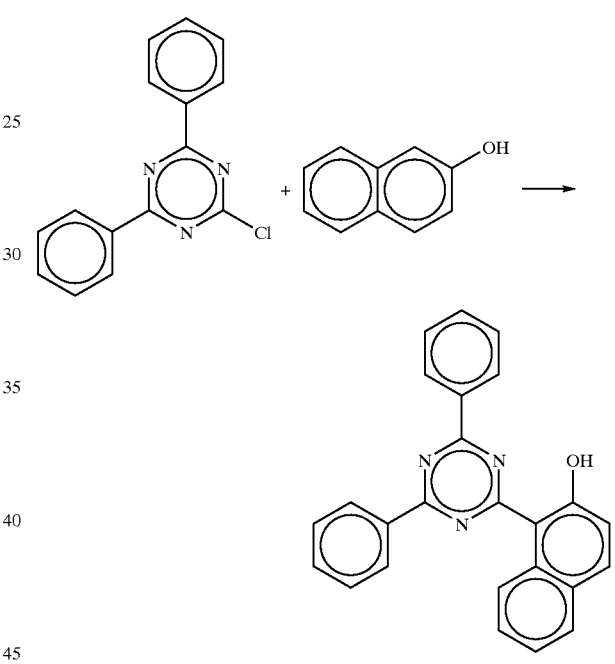

In a 2-neck round bottom flask equipped with a magnetic stirring bar, a condenser and a nitrogen inlet was added 5.4 g of 2,4-diphenyl-6-chloro-1,3,5-triazine (prepared by following the process disclosed in WO 00/29392), followed by 100 ml chlorobenzene and 2.9 g of 2-naphthol. To it was added 4 g AlCl$_3$ and the reaction mixture heated at 70° C. for 3 hours. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give 5.8 g of a product identified to be 2,4-diphenyl-6-(2-hydroxynaphthyl)-1,3,5-triazine on the basis of HPLC, NMR and mass spectroscopy. The UV spectrum confirmed it to be red-shifted UV absorber: $\lambda_{max}$ (nm) 280 ($\epsilon$: 55121); 329 ($\epsilon$: 9135); and 384 ($\epsilon$: 12542).

Example 3

Preparation of 2,4-bis(2,4-dimethylphenyl)-6-(2-hydroxynaphthyl)-1,3,5-triazine

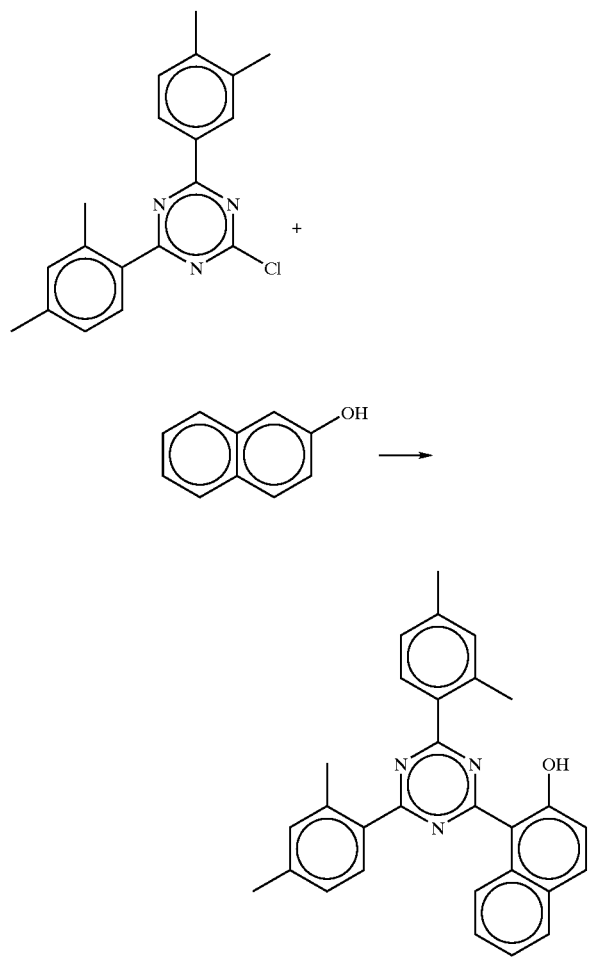

In a 2-neck round bottom flask equipped with a magnetic stirring bar, a condenser and a nitrogen inlet was added 3.2 g of 2,4-bis(2,4-dimethylphenyl)-6-chloro-1,3,5-triazine (prepared by following the process disclosed in WO 00/29392), followed by 25 ml chlorobenzene and 1.6 g of 2-naphthol. To it was then added 2 g $AlCl_3$ and the reaction mixture heated at 85° C. for 3 hours. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give a product identified to be 2,4-bis(2,4-dimethylphenyl)-6-(2-hydroxynaphthyl)-1,3,5-triazine on the basis of HPLC, NMR and mass spectroscopy. The UV spectrum confirmed it to be red-shifted UV absorber: $\lambda_{max}$ (nm) 280 ($\epsilon$: 59077); and 379 ($\epsilon$: 13204).

Example 4

A One-Pot Process for the Preparation of 2,4-bis(3,4-dimethylphenyl)-6-(2-hydroxynaphthyl)-1,3,5-triazine from Cyanuric Chloride

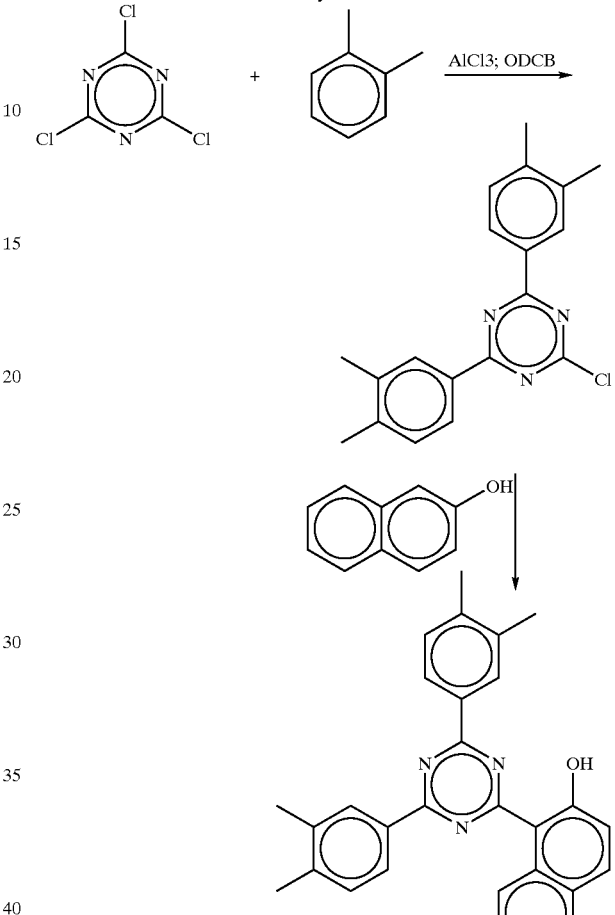

In a 3-neck round bottom flask equipped with a mechanical stirring, a condenser and a nitrogen inlet was added 9.2 g of cyanuric chloride followed by 100 ml of o-dichlorobenzene and 20 g $AlCl_3$ The mixture was cooled in an ice-bath, and 1.2 g of conc. HCl was added to it with stirring. The cooling bath was then removed and the mixture stirred at room temperature for 2 hr. The mixture was then cooled in an ice-bath and 10.1 g of o-xylene was slowly added to it maintaining the reaction mixture temperature between 5–10° C. The cooling bath was then removed and the mixture stirred at room temperature for about 16 hr. To the reaction mixture was then added 7.2 g of 2-naphthol, and the contents heated at 85° C. for 3 hours. The HPLC of the reaction mixture indicated the formation of a new major product and the completion of the reaction. The heating was discontinued, the reaction mixture was cooled to room temperature, and then quenched with water. ODCB was removed azeotropically. The precipitated solid was filtered, washed with water and dried to give a product identified to be 2,4-bis(3,4-dimethylphenyl)-6-(2-hydroxynaphthyl)-1,3,5-triazine on the basis of HPLC, NMR and mass spectroscopy.

Example 5

Preparation of 2,4-bis(2,4-dimethylphenyl)-6-(2,4-dihydroxynaphthyl)-1,3,5-triazine

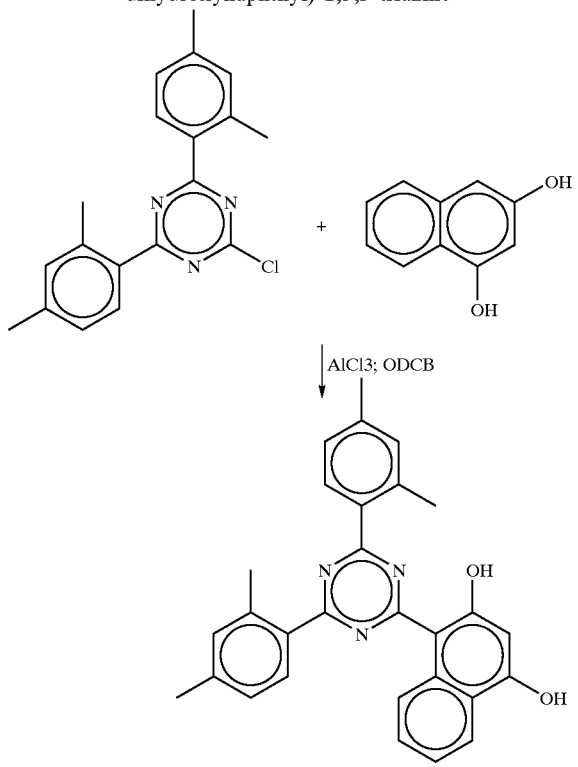

In a 2-neck round bottom flask equipped with a magnetic stirring bar, a condenser and a nitrogen inlet was added 3.2 g of 2,4-bis(2,4-dimethylphenyl)-6-chloro-1,3,5-triazine (prepared by following the process disclosed in WO 00/29392), followed by 15 mL o-dichlorobenzene and 1.6 g of 1,3-dihydroxynaphthalene. To it was then added 1.6 g $AlCl_3$ and the reaction mixture heated at 110–115° C. for 1 hour. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give a crude product, which was treated with hexane and filtered to give 3.8 g of a product identified to be 2,4-bis(2,4-dimethylphenyl)-6-(2,4-dihydroxynaphthyl)-1,3,5-triazine on the basis of HPLC, LC-UV, NMR and LCMS. The UV spectrum confirmed it to be red-shifted UV absorber: $\lambda_{max}$ (nm) 286 ($\epsilon$: 35035); and 391 ($\epsilon$: 18398).

Example 6

Reaction of 2,4-bis(2,4-dimethylphenyl)-6-(2,4-dihydroxynaphthyl)-1,3,5-triazine with 1-iodooctane: Synthesis of 2,4-bis(2,4-dimethylphenyl)-6-(2-hydroxy-4-octyloxynaphthyl)-1,3,5-triazine

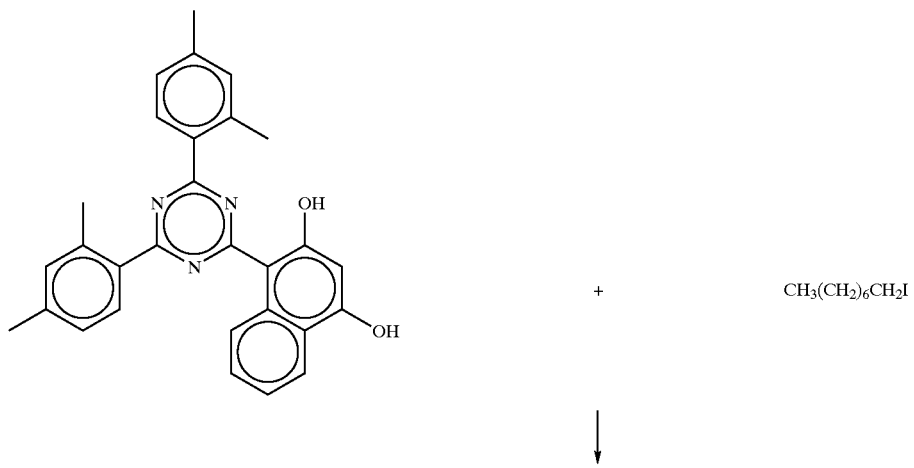

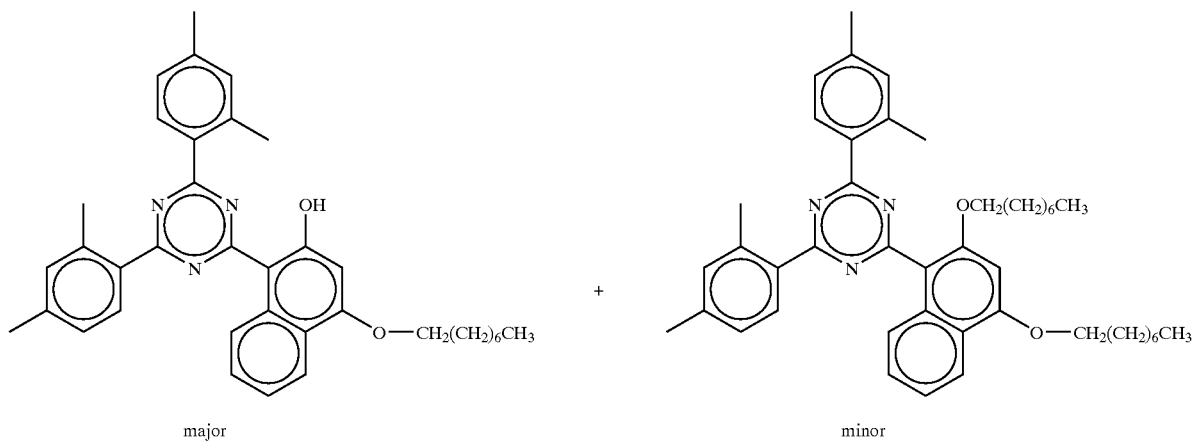

A mixture of 0.9 g 2,4-bis(2,4-dimethylphenyl)-6-(2,4-dihydroxynaphthyl)-1,3,5-triazine (Example 5), 0.48 g 1-iodooctane, 1.4 g anhydrous potassium carbonate, 0.2 g Aliquat 336 and 10 mL MIBK was heated to reflux for 4 hr. The reaction mixture was cooled to room temperature, diluted with methylene chloride, and filtered through Celite. The filtrate was concentrated under reduced pressure. The residue thus obtained was analyzed by HPLC, LCUV and LCMS to contain 2,4-bis(2,4-dimethylphenyl)-6-(2-hydroxy-4-octyloxynaphthyl)-1,3,5-triazine as a major product and 2,4-bis(2,4-dimethylphenyl)-6-(2,4-dioctyloxynaphthyl)-1,3,5-triazine as the minor product.

Example 7

Reaction of 2,4-bis(2,4-dimethylphenyl)-6-(2,4-dihydroxynaphthyl)-1,3,5-triazine with 1,8-diiodooctane: Synthesis of Dimeric Products

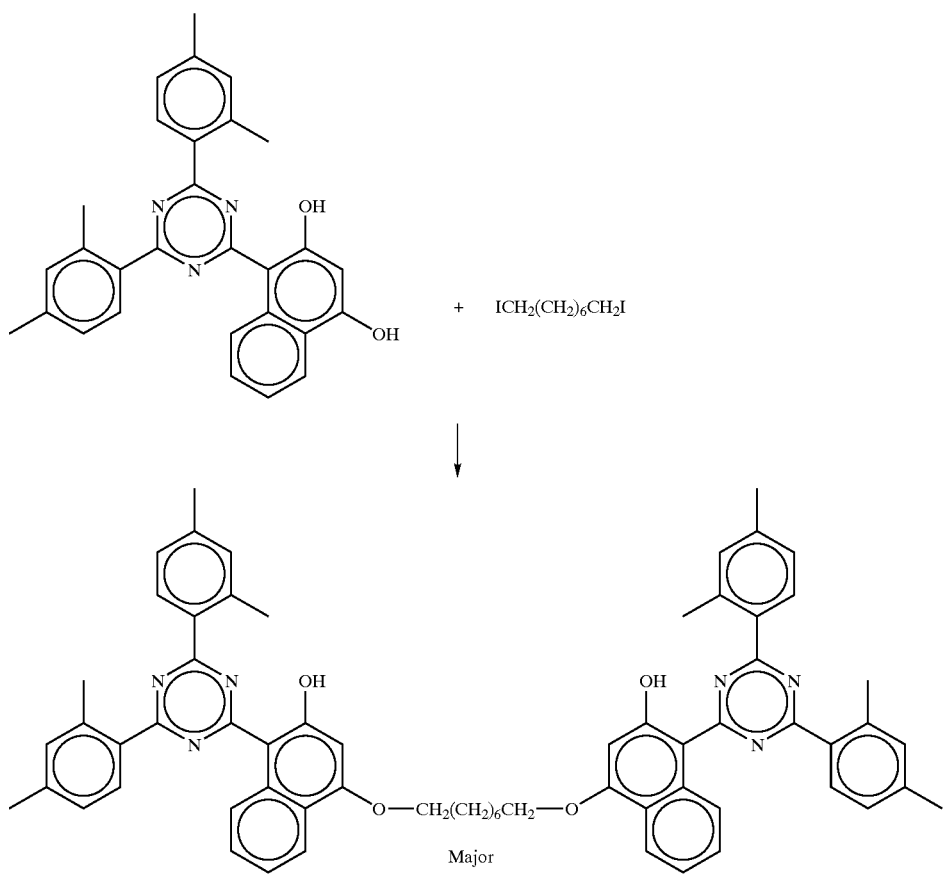

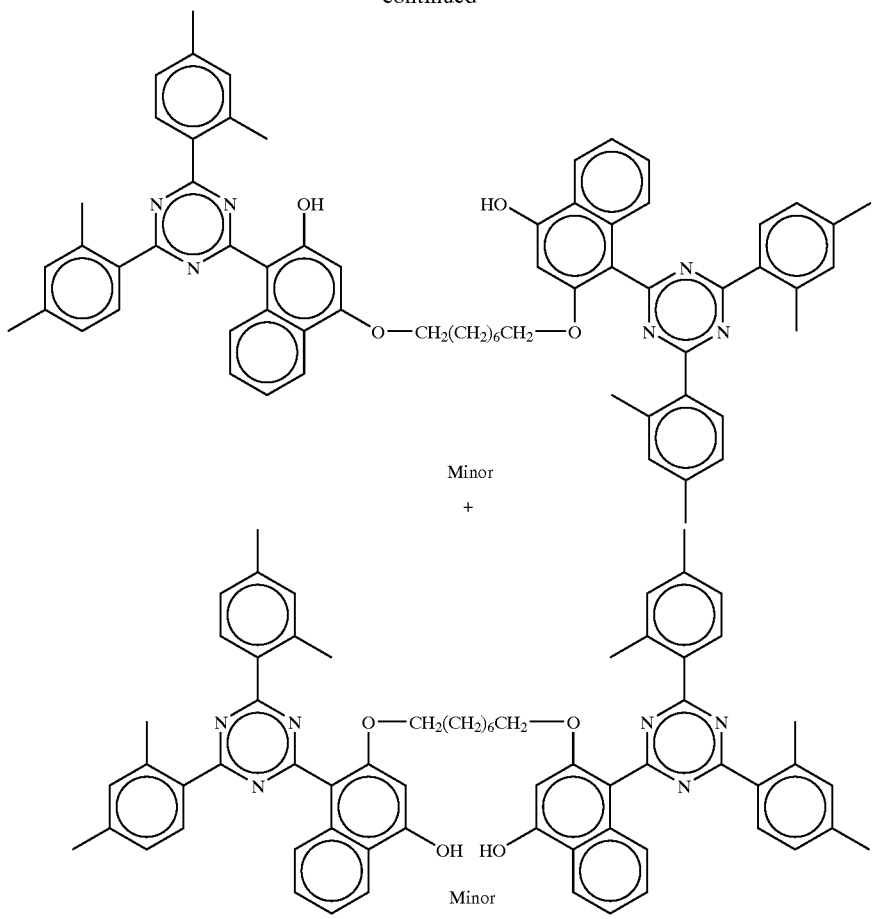

Minor

+

Minor

A mixture of 0.9 g 2,4-bis(2,4-dimethylphenyl)-6-(2,4-dihydroxynaphthyl)-1,3,5-triazine (Example 5), 0.37 g 1,8-diiodooctane, 1.4 g anhydrous potassium carbonate, and 10 mL MIBK was heated to reflux for 4 hr. The reaction mixture was cooled to room temperature, diluted with methylene chloride, and filtered through Celite. The filtrate was concentrated under reduced pressure. The residue thus obtained was analyzed by HPLC, LCUV and LCMS to contain 4-O, 4'-O dimer as the major product and 4-O, 2'-O and 2-O, 2'-O as the minor dimeric products.

Example 8

Reaction of 2,4-bis(phenyl)-6-(2-hydroxynaphthyl)-1,3,5-triazine with Adipoyl chloride: Synthesis of a Diester Dimer

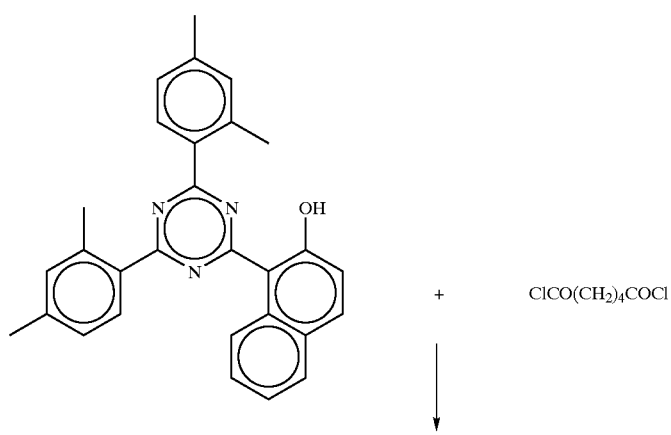

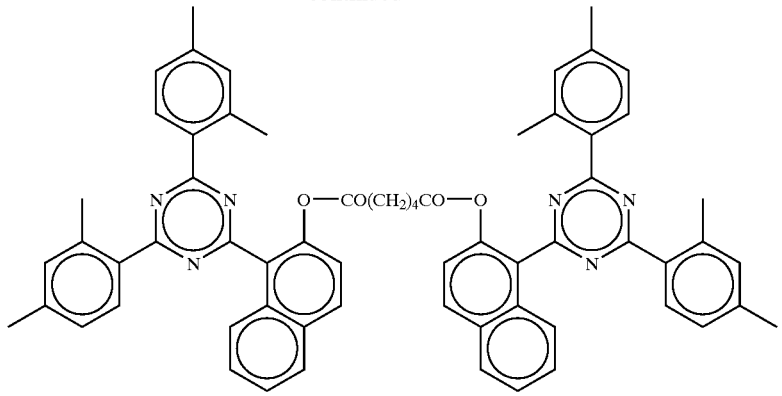

To a stirring mixture of 0.64 g of 2,4-bis(phenyl)-6-(2-hydroxynaphthyl)-1,3,5-triazine (Example 3) and 2 g of THF was added 0.064 g of sodium hydride at room temperature. To it was then added 0.068 g of adipoyl chloride, and the reaction mixture was then warmed to 50° C. and kept at this temperature for 16 hr. An additional 0.064 g of sodium hydride was added followed by 0.02 g of adipoyl chloride and stirred at room temperature for 2 hr. The reaction mixture was then quenched with water, and acidified with dilute HCl. The precipitated material was filtered, washed with water, and dried to give a crude product containing the desired diester dimer as the major product, as identified by HPLC, HPLC-UV, and LCMS.

Example 9

Preparation of 2,4-bis(2,4-dimethylphenyl)-6-(2-hydroxynaphthyl)-1,3,5-triazine and 2,4-bis(2,4-dimethylphenyl)-6-(2-methoxynaphthyl)-1,3,5-triazine

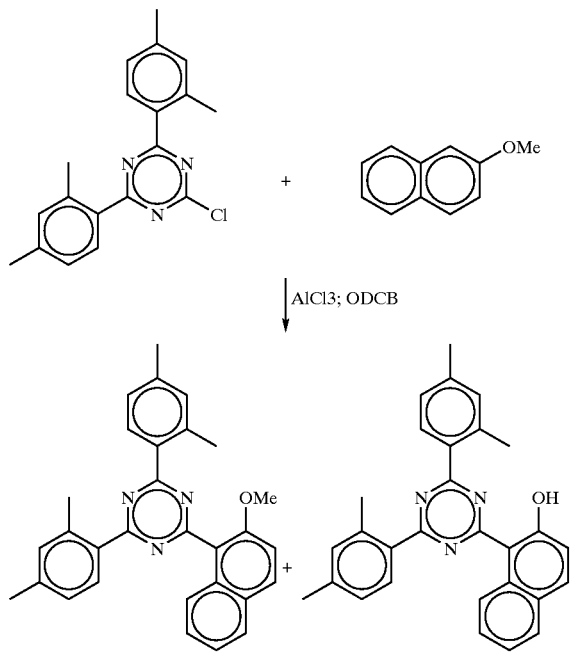

In a 2-neck round bottom flask equipped with a magnetic stirring bar, a condenser and a nitrogen inlet was added 3.2 g of 2,4-bis(2,4-dimethylphenyl)-6-chloro-1,3,5-triazine (prepared by following the process disclosed in WO 00/29392), followed by 15 mL o-dichlorobenzene and 1.58 g of 2-methoxynaphthalene. To it was then added 1.6 g AlCl₃ and the reaction mixture heated at 80–85° C. for 3 hours. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give a 3.8 g of a crude product, which was analyzed by HPLC, HPLC-UV, and LCMS to contain 2,4-bis(2,4-dimethylphenyl)-6-(2-hydroxynaphthyl)-1,3,5-triazine as the major product and 2,4-bis(2,4-dimethylphenyl)-6-(2-methoxynaphthyl)-1,3,5-triazine as the minor product.

Example 10

Preparation of 2,4-bis(2,4-dimethylphenyl)-6-(2,7-dihydroxynaphthyl)-1,3,5-triazine

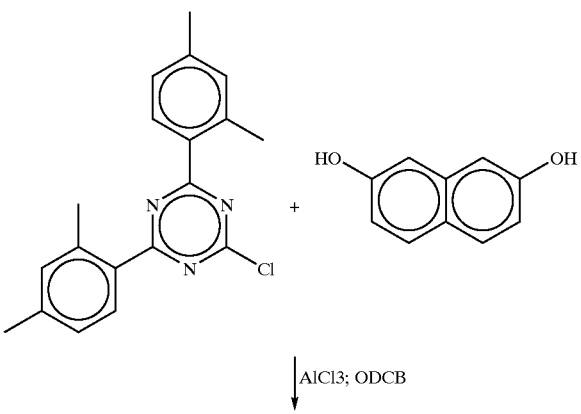

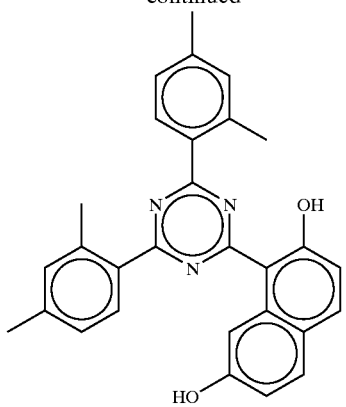

In a 2-neck round bottom flask equipped with a magnetic stirring bar, a condenser and a nitrogen inlet was added 3.2 g of 2,4-bis(2,4-dimethylphenyl)-6-chloro-1,3,5-triazine (prepared by following the process disclosed in WO 00/29392) followed by 15 mL o-dichlorobenzene and 1.6 g of 2,7-dihydroxynaphthalene. To it was then added 1.6 g AlCl$_3$ and the reaction mixture heated at 110–115° C. for 1 hours. The HPLC of the reaction mixture indicated the formation of a new product and the completion of the reaction. The heating was discontinued, the reaction mixture was cooled to room temperature, and then quenched with water. ODCB was removed azeotropically. The precipitated solid was filtered, washed with water and dried to give a 4.3 g of a crude product, which was analyzed by HPLC, HPLC-UV, and LCMS to contain mainly 2,4-bis(2,4-dimethylphenyl)-6-(2,7-dihydroxynaphthyl)-1,3,5-triazine.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A triazine compound of Formula I:

Formula I

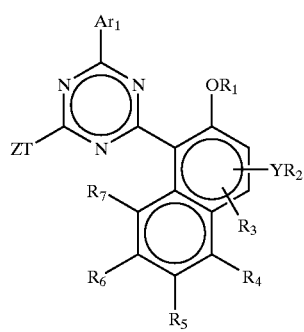

wherein $R_1$, $R_2$, are the same or different and each is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, COR, CONRR', and SO$_2$R;

$R_3$, $R_4$, $R_5$, $R_6$ and $R_7$ are the same or different and each is hydrogen, halogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, OR, NRR', CONRR', OCOR, CN, SR, SO$_2$R, SO$_3$H, SO$_3$M, wherein M is an alkali metal, R and R' are the same or different and each is hydrogen, alkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and Y is a direct bond, O, NR", or S, wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 7 to 24 carbons atoms;

wherein T is a direct bond, oxygen, NR' or sulfur;

and when T is oxygen, NR' or sulfur, Z is a hydrogen, substituted or unsubstituted alkyl of 1 to 24 carbon atoms, alkenyl of 2 to 24 carbon atoms, aryl of 6 to 24 carbon atoms, aralkyl of 7 to 24 carbon atoms, cycloalkyl of 5 to 24 carbon atoms, substituted or unsubstituted alkyl of 1 to 24 carbon atoms interrupted with at least one hetero atom, cycloalkyl of 5 to 24 carbon atoms interrupted with at least one hetero atoms, or Ar$_2$;

and when T is a direct bond, Z is a hydrogen, halogen, substituted or unsubstituted alkyl of 1 to 24 carbon atoms, alkenyl of 2 to 24 carbon atoms, aralkyl of 7 to 24 carbon atoms, cycloalkyl of 5 to 24 carbon atoms, cycloacyl of 5 to 24 carbon atoms, substituted or unsubstituted alkyl of 1 to 24 carbon atoms interrupted with at least one hetero atom, cycloalkyl of 5 to 24 carbon atoms interrupted with at least one hetero atoms, wherein Ar$_1$ and Ar$_2$ are each independently a radical of Formula II Formula II

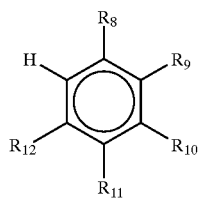

wherein $R_8$, $R_9$, $R_{10}$, $R_{11}$, and $R_{12}$ are the same or different and each is hydrogen, halogen, alkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', OCOR, and optionally with either of $R_8$ and $R_9$, $R_9$, and $R_{10}$, $R_{10}$ and $R_{11}$, or $R_{11}$ and $R_{12}$, taken together being a part of a saturated or unsaturated fused carbocyclic ring with the proviso that the radical of Formula II is not a naphthyl substituted with a hydroxyl group ortho to the point of attachment to the triazine ring.

2. The compound of claim 1, wherein T is a direct bond and Z is $Ar_2$.

3. The compound of claim 2, wherein $R_3$, $R_4$, $R_5$, $R_6$ and $R_7$ are hydrogen.

4. The compound of claim 3, wherein Y is an oxygen, $R_1$ is hydrogen, $R_2$ is hydrogen or an alkyl of 1 to 24 carbon atoms.

5. The compound of claim 3, wherein Y is a direct bond, and $R_1$ and $R_2$ are hydrogen.

6. The compound of claim 3, wherein $Ar_1$ and $Ar_2$ are selected from a group consisting of: phenyl, methylphenyl, dimethylphenyl, diphenyl, phenyl ether, tetralin, tert-butylphenyl, ethylphenyl, propylphenyl, isopropylphenyl, butylphenyl, isobutylphenyl, chlorophenyl, methoxyphenyl, hydroxyphenyl and combinations thereof.

7. A triazine compound of Formula III

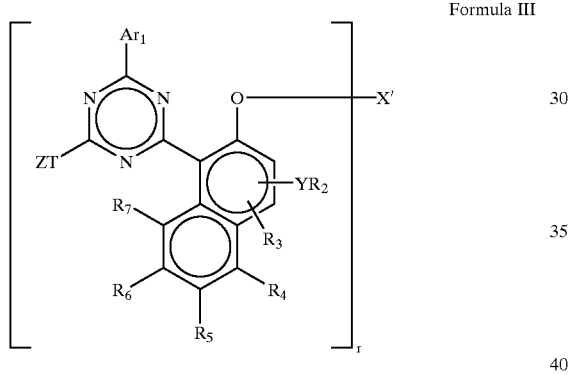

Formula III wherein T, Z, $Ar_1$ Y, $R_2$ to $R_7$ are defined as in claim 1;
r is 2 or 3;
when r is 2, X' is —CO—$R^{16}$—CO—, —$CO_2$—$R^{16}$— $CO_2$—, —$SO_2$—$R^{16}$—$SO_2$—, —CO—NH—$R^{17}$—NH—CO—, a polyoxyalkylene bridge member of formula —CO—$(CH_2)_u$—O—$(CH_2$—$(CH_2)_u$—O—$)_{mm}$—$(CH_2)_u$—CO—, or —COC($R^{21}$)$HCH_2NH(C_{nn}H_{2nn}O)_mC_{nn}H_{2nn}$—NHCH$_2$—C($R^{21}$)HCO—
when r=3, X' is:
—(—$CO_2$—$R^{16}$)$_3R^{19}$, —(—CONH—$R^{16}$)$_3R^{19}$, —(—$SO_2$—$R^{16}$)$_3R^{19}$; wherein
$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;
$R^{17}$ is $C_2$–$C_{10}$ alkylene, phenylene, naphthylene, methylenediphenylene or $C_7$–$C_{15}$ alkylphenylene;
$R^{19}$ is $C_3$–$C_{10}$alkanetriyl;
$R^{21}$ is hydrogen or $C_1$–$C_6$ alkyl;
mm is an integer from 2 to 60,
nn is an integer from 2 to 6, and
u is an integer from 1 to 4.

8. A triazine compound of Formula IV

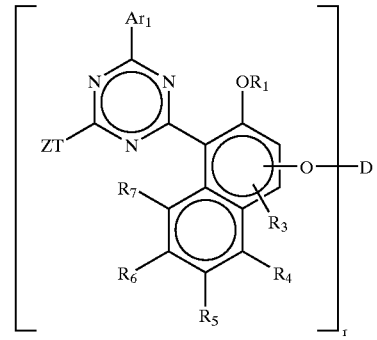

Formula IV wherein T, Z, $Ar_1$ Y, $R_1$ to $R_7$ are defined as in claim 1;
r is an integer between 2 and 4;
when r is 2, D is selected from the group consisting of $C_2$–$C_{16}$ alkylene, $C_4$–$C_{12}$ alkenylene, xylylene, $C_3$–$C_{20}$ alkylene which is interrupted by one or more oxygen atoms, hydroxy-substituted $C_3$–$C_{20}$ alkyl which is interrupted by one or more oxygen atoms, —$CH_2CH(OH)CH_2O$—$R^{15}$—$OCH_2CH(OH)CH_2$, —CO—$R^{16}$—CO—, —CO—NH—$R^{17}$—NH—CO—, —$(CH_2)_s$—COO—$R^{18}$—OCO—$(CH_2)_s$—
a polyoxyalkylene bridge member of the formula XX —$CH_2$—CH(OH)—$CH_2$—O—$(CH_2$—$(CH_2)_u$—O—$)_{mm}$—$CH_2$— CH(OH)—$CH_2$— (XX), a polyoxyalkylene bridge member of the formula XXI —CO—$(CH_2)_u$—O—$(CH_2$—$(CH_2)_u$—O—$)_{mm}$—$(CH_2)_u$—CO— (XXI), a polyoxyalkylene bridge member of the formula XXII —YY—O—CO$(CH_2)_u$—O—$(CH_2$—$(CH_2)_u$—O—$)_{mm}$—$(CH_2)_u$— COO—YY— (XXII), a polyoxyalkylene bridge member of the formula XXIII —$(CH_2)_{kk}$—CH($R^{21}$)—CO—$B_1$—$(C_{nn}H_{2nn}$—O—$)_{mm}C_{nn}H_{2nn}$— $B_1$—CO—CH($R^{21}$)—$(CH_2)_{kk}$— (XXIII), a polyoxyalkylene bridge member of the formula XXIV —COC($R^{21}$)$HCH_2NH(C_{nn}H_{2nn}O)_mC_{nn}H_{2nn}$—NHCH$_2$— C($R^{21}$)HCO— (XXIV), a polyoxyalkylene bridge member of the formula XXV —YY—O—CO—$(CH_2)_2$—NH—$(C_{nn}H_{2nn}$—O—$)_{mm}$—$C_{nn}H_{2nn}$— NH—$(CH_2)_2$COO—YY— (XXV), a polyoxyalkylene bridge member of the formula XXVI —$(C_{nn}H_{2nn}$—O—$)_{mm}$—$C_{nn}H_{2nn}$— (XXVI), and a polyoxyalkylene bridge member of the formula XXVII —CH($CH_3$)—$CH_2$—(O—CH($CH_3$)—$CH_2)_a$—(O—$CH_2$—$CH_2)_b$— (O—$CH_2$—CH($CH_3$))$_c$— (XXVII), wherein a+c=2.5 and b=8.5 to 40.5 or a+c 2 to 33 and b=0,
$R^{21}$ is hydrogen or $C_1$–$C_{16}$ alkyl, YY is unsubstituted or substituted $C_2$–$C_{20}$ alkyl,
kk is zero or an integer from 1–16,
mm is an integer from 2 to 60,
nn is an integer from 2 to 6,
u is an integer from 1 to 4;
$B_1$ is O or NH;
$R^{15}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl, or phenylene-XX-phenylene wherein XX is —O—, —S—, —SO$_2$—, —CH$_2$—, or —C(CH$_3$)$_2$—;
$R^{16}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl provided that when r is 3 the alkenyl has at least 3 carbons;
$R^{17}$ is $C_2$–$C_{10}$ alkyl, phenyl, naphthyl, diphenyl, or $C_2$–$C_6$ alkenyl, methylenediphenylene, or $C_4$–$C_{15}$ alkylphenyl; and
$R^{18}$ is $C_2$–$C_{10}$ alkyl, or $C_4$–$C_{20}$ alkyl interrupted by one or more oxygen atoms.
when r is 3, D is —[—(CH$_2$)$_s$—COO—]$_3$—R$^{19}$
and when r is 4, D is —[—(CH$_2$)$_s$—COO—]$_4$—R$^{20}$
wherein $R^{19}$ is $C_2$–$C_{10}$ alkanetriyl;
$R^{20}$ is $C_4$–$C_{10}$ alkanetetryl; and
s is 1–6.

9. A triazine compound of Formula V

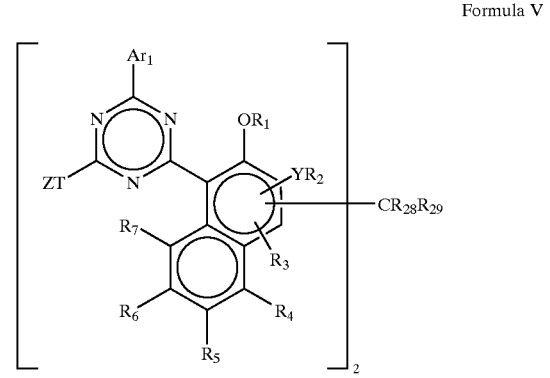

Formula V wherein T, Z, Ar$_1$ Y, R$_1$ to R$_7$ are defined as in claim 1;
and wherein R$_{28}$ and R$_{29}$ can be the same or different and each is independently a hydrogen, a $C_1$–$C_{20}$ alkyl, an aryl or substituted $C_1$–$C_{20}$ aryl.

10. A triazine compound of Formula VI

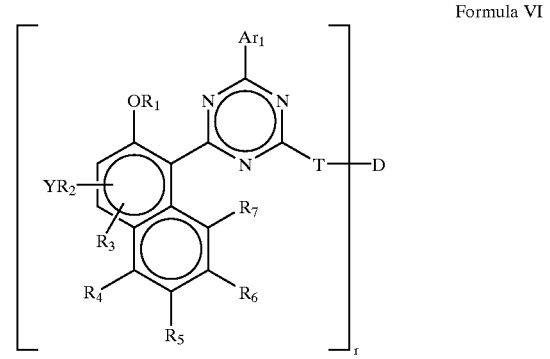

Formula VI wherein T, Ar$_1$, Y, R$_1$ to R$_7$ are defined as in claim 1;
r is an integer between 2 and 4;

when r is 2, D is selected from the group consisting of $C_2$–$C_{16}$ alkylene, $C_4$–$C_{12}$ alkenylene, xylylene, $C_3$–$C_{20}$ alkylene which is interrupted by one or more oxygen atoms, hydroxy-substituted $C_3$–$C_{20}$ alkylene which is interrupted by one or more oxygen atoms, —OOCR$^{14}$COO—, —CH$_2$CH(OH)CH$_2$O—R$^{15}$—OCH$_2$CH(OH)CH$_2$, —CO—R$^{16}$—CO—, —CO—NH—R$^{17}$—NH—CO—, and —(CH$_2$)$_s$—COO—R$^{18}$—OCO—(CH$_2$)$_s$—; and
when r is 3, D is —[—(CH$_2$)$_s$—COO—]$_3$—R$^{19}$
and when r is 4, D is —[—(CH$_2$)$_s$—COO—]$_4$—R$^{20}$
wherein $R^{19}$ is $C_3$–$C_{10}$ alkanetriyl and $R^{20}$ is $C_4$–$C_{10}$ alkanetetryl;
s is 1–6;
$R^{14}$ is $C_1$–$C_{12}$ alkyl or phenyl;
$R^{15}$ is $C_2$–$C_{10}$ alkylene phenylene or a phenylene-X$_2$-phenylene-group, wherein X$_2$ is —O—, —S—, —SO$_2$—, —CH$_2$—, or —C(CH$_3$)$_2$—;
$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;
$R^{17}$ is $C_2$–$C_{10}$ alkylene, phenylene, naphthylene, methylenediphenylene or $C_7$–$C_{15}$ alkylphenylene, and
$R^{18}$ is $C_2$–$C_{10}$ alkylene or $C_4$–$C_{20}$ alkylene which is interrupted by one or more oxygen atoms.

11. A triazine compound of Formula VII

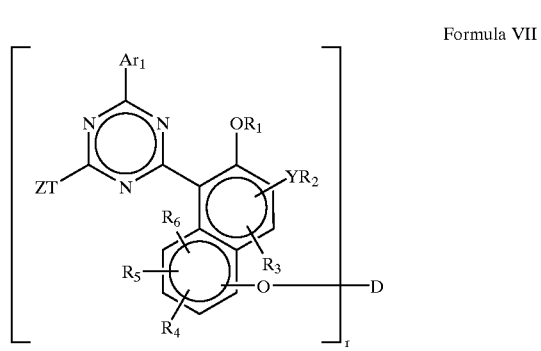

Formula VII wherein T, Z, Ar$_1$, Y, R$_1$ to R$_7$ are defined as in claim 1;
r is an integer between 2 and 4;
when r is 2, D is selected from the group consisting of $C_2$–$C_{16}$ alkylene, $C_4$–$C_{12}$ alkenylene, xylylene, $C_3$–$C_{20}$ alkylene which is interrupted by one or more oxygen atoms, hydroxy-substituted $C_3$–$C_{20}$ alkylene which is interrupted by one or more oxygen atoms, —OOCR$^{14}$COO—, —CH$_2$CH(OH)CH$_2$O—R$^{15}$—OCH$_2$CH(OH)CH$_2$, —CO—R$^{16}$—CO—, —CO—NH—R$^{17}$—NH—CO—, and —(CH$_2$)$_s$—COO—R$^{18}$—OCO—(CH$_2$)$_s$—; and
when r is 3, D is —[—(CH$_2$)$_s$—COO—]$_3$—R$^{19}$
and when r is 4, D is —[—(CH$_2$)$_s$—COO—]$_4$—R$^{20}$
wherein $R^{19}$ is $C_3$–$C_{10}$ alkanetriyl and $R^{20}$ is $C_4$–$C_{10}$ alkanetetryl;
s is 1–6;
$R^{14}$ is $C_1$–$C_{12}$ alkyl or phenyl;
$R^{15}$ is $C_2$–$C_{10}$ alkylene phenylene or a phenylene-X$_2$-phenylene-group, wherein X$_2$ is —O—, —S—, —SO$_2$—, —CH$_2$—, or —C(CH$_3$)$_2$—;
$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;

R$^{17}$ is C$_2$–C$_{10}$ alkylene, phenylene, naphthylene, methylenediphenylene or C$_7$–C$_{15}$ alkylphenylene, and R$^{18}$ is C$_2$–C$_{10}$ alkylene or C$_4$–C$_{20}$ alkylene which is interrupted by one or more oxygen atoms.

12. A method of stabilizing a material comprising the step of contacting said material with the triazine compounds of claims 1, 6, 7, 8, 9, 10 or 11.

13. The method of claim 12 wherein said material to be stabilized is selected from the group consisting of: polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, styrene acrylonitrile, acrylate styrene acrylonitrile, cellulosic acetate butyrate, cellulosic polymers, polyimides, polyamideimides, polyetherimides, polyphenylsulfides, polyphenylene oxide, polysulfones, polyethersulfones, polyvinylchlorides, polycarbonates, polyketones, aliphatic polyketones, thermoplastic TPO's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and mixtures thereof.

14. The method of claim 12 wherein the amount of said triazine compound is about 0.1 to about 20% by weight based on the material to be stabilized.

15. A composition comprising (a) the triazine compounds of claims 1, 6, 7, 8, 9, 10 or 11; and (b) at least one other additive selected from the group consisting of: UV-absorbers and light stabilizers, and antioxidants.

16. The composition of claim 15 wherein said at least one other additive is selected from the group consisting of 2-(2'-hydroxyphenyl)benzotriazoles, oxamides, 2-(2-hydroxphenyl)-1,3,5-triazines, 2-hydroxybenzophenones, sterically hindered amines and hindered phenol antioxidants.

17. The composition of claim 15 wherein said at least one additive is selected from the group consisting of: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4(1,1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; [R—CH$_2$CH—COO(CH$_2$)$_3$]$_2$ B where R=3'-tert-butyl-4'-hydroxy-5'-2H-benzotriazol-2-ylphenyl; bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed isooctyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy4- tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy-4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of β-(3,5-di-tert-butyl-4-hydroxyphenyl)propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

18. The composition of claim 15 further comprising a material to be stabilized, said material selected from the group consisting of: polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, styrene acrylonitrile, acrylate styrene acrylonitrile, cellulosic acetate butyrate, cellulosic polymers, polyimides, polyamideimides, polyetherimides, polyphenylsulfides, polyphenylene oxide, polysulfones, polyethersulfones, polyvinylchlorides, polycarbonates, ipolyketones, aliphatic polyketones, thermoplastic TPO's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and mixtures thereof.

19. The composition of claim 15 wherein the amount of said triazine compound to said at least one other additive is from about 500:1 to about 1:500 by weight.

* * * * *

UNITED STATES PATENT AND TRADEMARK OFFICE
CERTIFICATE OF CORRECTION

PATENT NO. : 6,800,757 B2
DATED : October 5, 2004
INVENTOR(S) : Ram Baboo Gupta et al.

It is certified that error appears in the above-identified patent and that said Letters Patent is hereby corrected as shown below:

Column 34,
Line 35, replace the entire line to read
-- —CO—$(CH_2)_u$—O—$(CH_2$—$(CH_2)_u$—O—$)_{mm}$—$(CH_2)_u$—CO—     (XXI), --
Line 65, replace "b=8.5to" with -- b=8.5 to -- and replace "a+c 2to" with -- a+c 2 to --

Column 35,
Line 9, after "XX-phenylene" insert -- , --
Line 10, after "—O—, —S—" insert -- m --
Line 23, replace "$C_2$-$C_{10}$" with -- $C_3$-$C_{10}$ --

Column 38,
Line 10, after "methylenebis[4" insert -- - --

Column 40,
Line 14, replace "ipolyketones" with -- polyketones --

Signed and Sealed this

Seventh Day of June, 2005

JON W. DUDAS
*Director of the United States Patent and Trademark Office*